United States Patent [19]

Hoenig et al.

[11] Patent Number: 5,152,288
[45] Date of Patent: Oct. 6, 1992

[54] APPARATUS AND METHOD FOR MEASURING WEAK, LOCATION-DEPENDENT AND TIME-DEPENDENT MAGNETIC FIELDS

[75] Inventors: Eckhardt Hoenig, Erlangen; Helmut Reichenberger, Eckental; Siegfried Schneider, Erlangen, all of Fed. Rep. of Germany

[73] Assignee: Siemens Aktiengesellschaft, Munich, Fed. Rep. of Germany

[21] Appl. No.: 774,635

[22] Filed: Oct. 9, 1991

Related U.S. Application Data

[63] Continuation of Ser. No. 412,217, Sep. 25, 1989, abandoned.

[30] Foreign Application Priority Data

Sep. 23, 1988 [EP] European Pat. Off. ........ 88115716.8

[51] Int. Cl.$^5$ .............................................. A61B 5/05
[52] U.S. Cl. .................. 128/653.1; 128/731; 324/248; 324/262
[58] Field of Search .............. 128/653 R, 731, 732; 324/249, 262

[56] References Cited

U.S. PATENT DOCUMENTS

| | | | |
|---|---|---|---|
| 4,079,730 | 3/1978 | Wikswo, Jr. et al. .......... | 128/653 R |
| 4,275,744 | 6/1981 | Thornton et al. .................. | 128/731 |
| 4,736,751 | 4/1988 | Gevins et al. ...................... | 128/732 |
| 4,744,029 | 5/1988 | Raviv .................................. | 128/731 |
| 4,771,239 | 9/1988 | Hoenig ............................ | 128/653 R |
| 4,827,217 | 5/1989 | Paulson ............................ | 128/653 R |
| 4,889,124 | 12/1989 | Schneider ........................ | 128/653 R |

FOREIGN PATENT DOCUMENTS

| | | |
|---|---|---|
| 0277283 | 10/1987 | European Pat. Off. . |
| 8715844 | 5/1988 | Fed. Rep. of Germany . |
| 8807834 | 10/1988 | PCT Int'l Appl. ............. 128/653 R |

OTHER PUBLICATIONS

Odehral et al. "Low Level SQUID magnetometry", Cryogenics, vol. 18 No. 7 (Jul. 1978) pp. 427–431.
Brenner et al. "SQUID System for Detecting Evoked Magnetic Fields", Proc. 14th. Intl. Conf. on Low Temp. Phys., (1975) pp. 266–269.
Cohen et al., "Magnetocardiograms Taken Inside a Shielded Room", Applied Physics Letters (1970) pp. 278–280.
"Biomagnetismus Singals aus Dem Korper", Honshein, Bid Der Wissenschaft, No. 8, 1986 pp. 76–83.
"Construction and Performance of the Otaniemi Magnetically Shielded Room", Kelhä, Biomagnetism 1981, pp. 33–50.
"Design and Performance of 14-Channel Neuromagnetometer", Crum et al., Biomagnetic Tech. Publ., 1985.
"MCG Inverse Solution: Influence of Coil Size, Grif Size, Number of Coils, and SNR", Abraham-Fuchs et al., IEEE Transactions on Biomedical Engineering, 1988, pp. 573–576.
"Design, Contruction, and Performance of a Large-Volume Magnetic Shield," Kelha et al., IEEE Transactions on Magnetics vol. MAG-18, No. 1, Jan. 1982, pp. 260–270.
"Large-Area Low-Noise Seven-Channel DC SQUID Magnetometer for Brain Research", Knuutila et al., Review of Scientific Instruments, vol. 58, No. 11 (1987) pp. 2145–2156.
"V Berlin Magnetically Shielded Room (BMSR)," Mager, Proceedings of the Third International Workshop on Biomagnetism, May 1980, pp. 51–79.
"Characterization of Brain Noise with a Seven-Channel SQUID Magnetometer," Hamalainen et al., Proceedings of the 18th International Conference on Low Temperature Physics, Japanese Journal of Applied Physics, vol. 26, Supplement 26-3 (1987) pp. 1569–1560.

*Primary Examiner*—Ruth S. Smith
*Attorney, Agent, or Firm*—Hill, Van Santen, Steadman & Simpson

[57] ABSTRACT

An apparatus for measuring weak, location-dependent and time-dependent magnetic fields emitted from a source situated in an examination subject includes a sensor arrangement having at least ten gradiometers of the first order, each gradiometer being inductively coupled to a DC-SQUID. The sensor arrangement and the examination subject are disposed in a room which shields the examination subject and the sensor arrangement from magnetic fields. The room has a shielding factor of at least 10 for magnetic alternating fields having a frequency of 0.5 Hz, the shielding factor increasing with increasing frequency. A method for operating the apparatus is also disclosed.

12 Claims, 9 Drawing Sheets

APPARATUS AND METHOD FOR MEASURING WEAK, LOCATION-DEPENDENT AND TIME-DEPENDENT MAGNETIC FIELDS

This is a continuation of application Ser. No. 412,217, filed Sep. 25, 1989, now abandoned.

BACKGROUND OF THE INVENTION

1. Field of the Invention

The invention is directed to an apparatus for measuring weak, location-dependent and time-dependent magnetic fields which emanate from a source situated in an examination subject; the invention is also directed to a method for the operation of such an apparatus.

2. Description of the Prior Art

Devices are gaining increasing significance in medical diagnostics for measuring biomagnetic signals, i.e. signals that emanate from sources situated in the body of a life form (see the periodical "Bild der Wissenschaft", No. 8, 1986, pages 76 through 83). Such devices must be able to mensurationally acquire the extremely weak biomagnetic signals, for example the magnetic fields emanating from the human brain or from the human heart, whose field strength is on the order of magnitude of $10^{-12}T$ and below. These signals are required in medical diagnostics for producing magnetoencephpalograms (MEG) and magnetocardiograms (MCG), which offer the advantage over electroencephalograms (EEG) and electrocardiograms (ECG) that the distortions occurring therein, caused by the passage of the currents to be acquired through the human tissue, are noticeably lower. Of particular interest for experimental research and diagnostics are the magnetic fields produced in the brain of a life form provided as examination subject which, for example, arise due to acoustic and optical stimulation of the senses of the examination subject.

Devices of the species initially cited usually have a bearing means for the acceptance of the examination subject, a sensor arrangement for measuring magnetic fields, a holder for the sensor arrangement, means for adjusting the bearing means and the sensor arrangement relative to one another, and an electronic means for amplifying and evaluating the signals deriving from the sensor arrangement, the electronic means comprises a data processing system for evaluating the acquired signals and an input means for measured results. A chamber that surrounds the bearing means and the sensor arrangement can be provided for shielding magnetic fields (shielded room). As a rule, the sensor arrangement comprises one or more gradiometers (field measuring coils with allocated compensation coils) of the first or of a higher order, a plurality of SQUIDs (superconducting quantum interference devices) corresponding in number to the plurality of gradiometers, whereby every gradiometer is inductively coupled to one of the SQUIDs. The sensor arrangement also includes a cryostat, wherein a temperature at which the SQUIDs and the gradiometers are superconductive prevails. As a rule, the cryostat is filled with liquid helium, i.e. a temperature of 4.2° K. is present in the interior thereof.

It is theoretically possible with apparatus of this species to identify the local field strength of the magnetic field emanating from a source dependent on time. It is also possible, by suitable evaluation of the signals derived from the sensor arrangement upon consideration of the position of the sensor arrangement relative to the examination subject, to identify, for example, the spatial position of a source of a magnetic field situated in the inside of the examination subject. This is done on the basis of suitable calculating methods that sequence at the data processing system to which the signals of the sensor arrangement are supplied.

Essentially two problems arise. In view of the low field strength of the magnetic fields to be measured, first, the sensor arrangement must supply high-quality signals that are free of disturbances produced by environmental influences, for example noise fields, radio frequency fields or mechanical vibrations. Second, the signals derived from the sensor arrangement must be processed in the data processing system such that an sufficiently exact coincidence of the results acquired with the data processing system and the actual conditions is present. There is a relationship between the two problems insofar as only the solution of both problems can lead to results that coincide with reality with sufficient precision.

The efforts previously undertaken to resolve the former problem were directed at least to the sensor arrangement and to the shielded room.

For example, sensor arrangements were developed that contain extremely well-balanced gradiometers of the second order, that are balanced to $10^{-4}$ or better, i.e. their sensitivity is reduced by the factor $10^4$ or more for uniform fields ("Design and Performance of a 14-Channel Neuromagnetometer", Crum et al, 1985). The sensor arrangement disclosed therein contains a total of fourteen gradiometers of the second order arranged into cryostats, in groups of seven gradiometers each. The manufacture and operation of such a well-balanced sensor arrangement cause considerable outlay and costs. Even the manufacture of individual gradiometers of the second order having the aforementioned low sensitivity for uniform fields involves a considerable outlay. Additional measures for reducing interactive electrical and mechanical disturbances between the individual gradiometers and between the gradiometers and their mount must be undertaken in the arrangement and operation in an array of gradiometers of the second order. The outlay for the measuring instrument described in the publication is thereby further increased in that measures for measuring magnetic noise fields and for electronic compensation of the measured noise fields are undertaken.

Further, a shielded room executed in seven-shell structure having extremely high shielding effect for magnetic fields has been developed whose inner shell is formed of copper, whereas the remaining shells are composed of mu-metal (A. Mayer, "The Berlin Magnetically Shielded Room (BMSR)", Biomagnetism, Walter de Gruyter & Co., Berlin-N.Y., 1981, pages 73 ff). This structure leads, first, to an extremely high shielding effect of $3 \times 10^4$ at 0.4 Hz, $3 \times 10^5$ at 5 Hz, $1.5 \times 10^5$ at 50 Hz and $10^6$ at higher frequencies, and thereby enables the employment the uncompensated measuring coils. This is achieved, however, on the basis of extremely high outlay for the structure and corresponding costs.

A further shielded room having extremely high shielding effect is described in V. Kelha, "Construction and Performance of the Otaniemi Magnetically Shielded Room", in Biomagnetism, 1981, pages 33 through 50. Comparatively high shielding factors are achieved with this shielded room that includes three mu-metal shells, each of which is enclosed between two aluminum layers. Controlled, active shielding is also provided as well as further shielding measures on the basis of what is referred to as the shaking method. Here, too, however, the outlay for constructing a total of nine shells and for the operation of the room is considerable. In addition, an effect that deteriorates the quality of the signals results because the innermost layer of the shielded room is composed of aluminum and, thus, disturbing influences due to eddy currents in the aluminum shell appear.

The sensor arrangements and shielded rooms of the prior art, accordingly, do not allow an apparatus of the species initially cited to be realized that is able to supply measured signals with the required quality.

The fundamental aspects of an operating method for apparatus of the species initially cited are disclosed in U.S. Pat. No. 4,736,751. This method assumes a sensor arrangement of at least thirty-two gradiometers; however, no details are provided regarding what quality the signals of gradiometers must have for the known method and with what apparatus signals can be acquired having adequate quality.

SUMMARY OF THE INVENTION

It is an object of the present invention to provide an apparatus of the species initially cited such that meaningful signals, after processing with an electronic data processing system leads to usable results, are obtained with optimally little apparatus outlay.

It is also an object of the present invention to describe a method for the operation of an apparatus of the species initially cited that allows results that correspond with optimum precision to reality to be obtained on the basis of signals obtained with optimally little apparatus outlay.

The above objects are achieved in an apparatus having a bearing means for the acceptance of the examination subject and a sensor arrangement which includes an array of at least ten gradiometers of the first order, whereby each gradiometer has a field coil and a corresponding compensation coil and the field coils of the gradiometer are arranged in a sensor surface, and which further includes an array of a plurality of DC-SQUIDs corresponding in number to the plurality of gradiometers, whereby each gradiometer is inductively coupled to one of the DC-SQUIDs. A vessel containing the gradiometers and the corresponding DC-SQUIDs is provided wherein a temperature prevails at which the DC-SQUIDs and the gradiometers are superconductive. The apparatus further includes a holder for the sensor arrangement and means for adjusting the bearing means and the sensor arrangement relative to one another such that the sensor arrangement can be aligned to desired zones of the examination subject. The apparatus also includes a room surrounding the bearing means and the sensor arrangement for shielding magnetic fields (shielded room), that has a shielding factor of at least ten for magnetic alternating fields having a frequency of 0.5 Hz, a shielding factor of at least 100 for magnetic alternating fields having a frequency of 5 Hz, and a shielding factor of at least 1,000 for magnetic alternating fields having a frequency of 50 Hz and above. An electronic means is provided for amplifying and evaluating the signals of the gradiometers, which includes an amplifier arrangement connected to the DC-SQUIDs, an analog-to-digital converter connected to the amplifier arrangement and an electronic data processing system connected thereto. The amplifier arrangement has a plurality of amplifier channels corresponding in number to the plurality of gradiometers, each of these amplifier channels being connected to one of the DC-SQUIDs. The data processing system comprises a display for visually portraying results of the evaluation of the signals of the gradiometers.

Despite the employment of gradiometers of the first order in the sensor arrangement and despite the employment of a shielded room whose shielding factor lies considerably below the shielding factor of shielded rooms usually employed, it has been surprisingly shown that such an apparatus—given the condition that the sensor arrangement comprises an array of at least ten gradiometers of the first order—supplies signals of such high quality that the prerequisites are established for obtaining results that correspond extremely well to reality. The apparatus of the invention can be realized with comparatively little outlay since gradiometers of the first order are very easy to manufacture in comparison to gradiometers of a higher order, and an exact balancing the gradiometers can be omitted in the apparatus of the invention. It is thus sufficient that the gradiometers be balanced to less than $2 \times 10^{(-2)}$ for uniform magnetic fields. This can be obtained without having to undertake special measures in the manufacture of the gradiometers. The outlay for the shielded room is also comparatively low given the apparatus of the invention since the invention does not require an extremely high shielding effect. For high-frequency alternating fields, the shielded room should preferably have a shielding factor (field strength outside the shielded room with reference to the field strength inside the shielded room) on the order of magnitude of 1,000. The known DC-SQUIDs used in the invention differ from known RF-SQUIDs in that DC-SQUIDs have a lower thermal noise than RF-SQUIDs.

A sensor arrangement having seven gradiometers of the first order and a corresponding number of DC-SQUIDs is disclosed in M.S. Hamalainen et al, "Characterization of Brain Noise with a seven channel SQUID Magnetometer", Japanese Journal of Applied Physics, Vol. 26 (1987), Supplement 26-3, pages 1569 through 1570. As investigations have shown, systems with seven channels in a coherent sensor surface require the serial pick-up of the signals in different positions of the sensor arrangement so that a source can be acquired. What is needed, however, is a system that allows the simultaneous pick-up of all signals needed for a source acquisition. Given the presence of noise components in the signal, the minimum number of channels required for this purpose is ten.

In an advantageous modification of the invention, the sensor arrangement contains at least twelve gradiometers of the first order, with only gradiometers having the same structure being used. These modifications allow measured results corresponding very well to reality to be obtained using a calculating method of relatively low complexity, since increasing the number of gradiometers by two has a noticeably enhancing effect on the precision of the results.

A further modification of the invention provides that the shielded room is fashioned such that the inhomogeneity of the magnetic residual field present in the interior of the shielded room during a measurement is lower that 100 nT/m. This inhomogeneity of the residual field and the specified shielding factors can be achieved when the shielded room is constructed of two shells, whereby the inner shell is formed of mu-metal, whereas the outer shell is formed of aluminum. Such a shielded room, moreover, offers the advantage that the inner shell of mu-metal shields the interior of the shielded room containing the examination subject and the sensor arrangement from the magnetic noise that is produced by eddy currents in the outer shell formed of aluminum. Further, such a shielded room has a shielding factor of at least 1,000 for high-frequency alternating fields (frequencies above 1 kHz). In a further embodiment of the invention, the shielded room can be provided with a demagnetization means that charges the shielded room with a demagnetization field with which the demagnetization of the shielded room can be reduced over at least four orders of magnitude proceeding from the saturation field strength for mu-metal. The flux density and the inhomogeneity of the residual field present in the inside of the shielded room are further reduced by this measure. An especially advantageous embodiment is that of a shielded room constructed of three shells, with a further, outer mu-metal shell applied in addition to the two-shell embodiment.

Another modification of the invention provides that the sensor arrangement and the bearing means are held such that the distance changes occurring between the sensor arrangement and the bearing means as a consequence of mechanical excitation during a measurement are less than 100 $\mu$m. The term "mechanical excitation" as used herein encompasses all influences that can lead to undesired distance changes between the sensor arrangement and the bearing means, for example, vibrations of the floor or sound waves. Only extremely slight distance changes as a consequences of mechanical excitation occur between the sensor arrangement and the bearing means when, in another embodiment of the invention, a foundation for the shielded room is provided on which the holder of the sensor arrangement and the bearing means are attached separately from one another. The foundation is preferably seated on a sand bed and a direct mechanical connection both between the holder of the sensor arrangement and the shells of the shielded room, as well as between the bearing means and the shells of the shielded room, is avoided.

In a preferred embodiment, the gradiometers are axial gradiometers whose sensitivity of uniform magnetic fields is less than about $2 \times 10^{-2}$. What is meant by an axial gradiometer is a gradiometer whose field and compensation coil have a common center axis. The employment of axial gradiometers offers the advantage that a higher number of gradiometers can be arranged in a prescribed area than, for example, given planar gradiometers wherein the field and compensation coil lie side-by-side in a surface. The signal intensity, moreover, is correspondingly higher.

In a further modification of the invention, the field coils of the gradiometers each surround an area of at least 3.5 cm$^2$, which is preferably approximately circular. The sensor surface containing the field coils of the gradiometers can thus be fashioned approximately circular, and has a diameter of at least 8 cm. These features yield the advantage that a measuring surface sufficient for surface-covering acquisition of a source is available, and the required minimum number of gradiometers can be arranged therein.

In another modification of the invention, the amplifier arrangement includes a pre-amplifier followed by a lock-in amplifier, whereby the number of pre-amplifiers and lock-in amplifiers corresponds to the number of amplifier channels of the amplifier arrangement.

In an especially advantageous embodiment, an isolating amplifier is connected in each amplifier channel, either between the pre-amplifier and the lock-in amplifier or following the lock-in amplifier. The isolating amplifier serves the purpose of undertaking a voltage separation between the amplifiers. Ground loops are thereby avoided.

Each amplifier channel can be followed by a comb filter tuned to the line frequency, and the whole multiples thereof, to be able to filter corresponding disturbances out of the signals. Moreover, an anti-aliasing filter can be provided in every amplifier channel between the isolating amplifier and the analog-to-digital converter in order to avoid the appearance of artifacts in the analog-to-digital conversion.

When a life form is the examination subject, means for measuring at least one physiological function, for example the heart activity (ECG) of the life form, can be connected to the data processing system in addition to the measurement of the magnetic signals. There is thus the possibility of interpreting the results obtained dependent on the measured physiological function. Moreover, means for stimulating the senses of the life form can be connected to the data processing system so as to be able to evaluate the effects of a stimulation of the senses of the life form on the results.

Another modification of the invention includes that means for positioning the examination subject on the bearing means in a defined position relative to the bearing means and means for identifying the spatial position of the sensor arrangement relative to the bearing means are provided. On the basis of corresponding data, the data processing system permits identification of the spatial position of the sensor arrangement with reference to the examination subject, which is of particular significance for obtaining exact results.

The method for operating an apparatus of the type disclosed herein includes the steps of storing the signals derived from the gradiometers in the data processing system in digitized form as a function of the time over a measuring time span, calculating data concerning the spatial position of the sensor arrangement relative to the examination subject calculated for the measuring time span in the data processing system on the basis of the data derived from the means for identifying the spatial position of the sensor arrangement relative to the bearing means and the data regarding the spatial position of the sensor arrangement relative to the examination subject and storing the data in digitized form in the data processing system as a function of the time. Based on a model of the examination subject, the data processing system uses the signals derived from the gradiometers and the data relating to the spatial position of the sensor arrangement relative to the examination subject to optionally calculate the following for a source of magnetic signals: (a) the chronological course of the magnetic flux density of the source, (b) the chronological course of the magnetic flux density of the source (Q) in a presentation corresponding to the arrangement of the gradiometers, (c) a field line chart for a prescribed point in time in the measuring time span, in which field line chart lines of identical magnetic flux density belonging to the source are contained for a freely definable plane, or (d) the spatial position of the source in a prescribed point in time in the measuring time span. The measured results are supplied as an output to a display.

Proceeding from the signals of an apparatus having ten (but preferably, twelve) gradiometers, the method of the invention permits results to be obtained that largely correspond to reality. A sphere or a half-space of uniform conductivity can thereby form the basis—as model of the examination subject—of the calculation to be undertaken with the data processing system. The calculations undertaken with the data processing system are based on the fact that the preferred examination zones in life forms are the brain and heart, whereby the brain is modeled as a conductive sphere and the heart, together with the thorax, is modeled as a conductive half-space in which the sources of magnetic signals are respectively situated as a current dipole.

The output of the results in the form of the chronological course of the magnetic flux density of the source is particularly applicable when the quality of the signals is to be judged based on curve shape and chronological course and also diagnostic statements corresponding to traditional electrical method (EEG, ECG) are to be acquired. By contrast, the output of the results in the form of field line charts is particularly advantageous when the planar distribution of the signals is considered, particularly in view of a selection of sections accessible to a farther-reaching interpretation as well as for the portrayal of the dynamics of physiological events. Generating the position of the spatial source as an output will be selected when conclusions regarding the space-time course of body functions, or even regarding therapy measures derived therefrom, are to be drawn from the examination. Examples are the acquisition of excitation foci given focal epilepsy of the brain or the stimulus conduction of the heart.

A preferred embodiment of the method of the invention provides that an anatomical image of the examination subject produced with a tomography apparatus, for example with a nuclear magnetic resonance tomography apparatus, is stored in the data processing system and that the output of the results ensues such that the anatomical image, preferably a three-dimensional image of the examination subject, is portrayed, with the position of the source being entered therein for a prescribed point in time of the measuring time span. This way of displaying the results is especially illustrative and informative. A sequence of preferably three-dimensional anatomical images, into which at least the spatial position of the source is respectively entered, can be portrayed as an output for successive points in time within the measuring time span.

When a life form is the examination subject, the senses of the life form can be stimulated during the measuring time span, for example by optical and/or acoustical stimulation, and the output of results ensues for points in time within the measuring time span during which the senses of the life form are stimulated. Moreover, a periodic physiological function of the life form can be measured during the measuring time span and stored in the data processing system in digitized form as a function of time. In a modification of the invention, it is then possible that the output of results ensues for points in time during which the physiological function of the life form has a defined value. It is thus possible to judge the obtained results dependent on a stimulation of the senses of the life form or on a physiological function of the life form.

DESCRIPTION OF THE PREFERRED EMBODIMENTS

Figure 1:
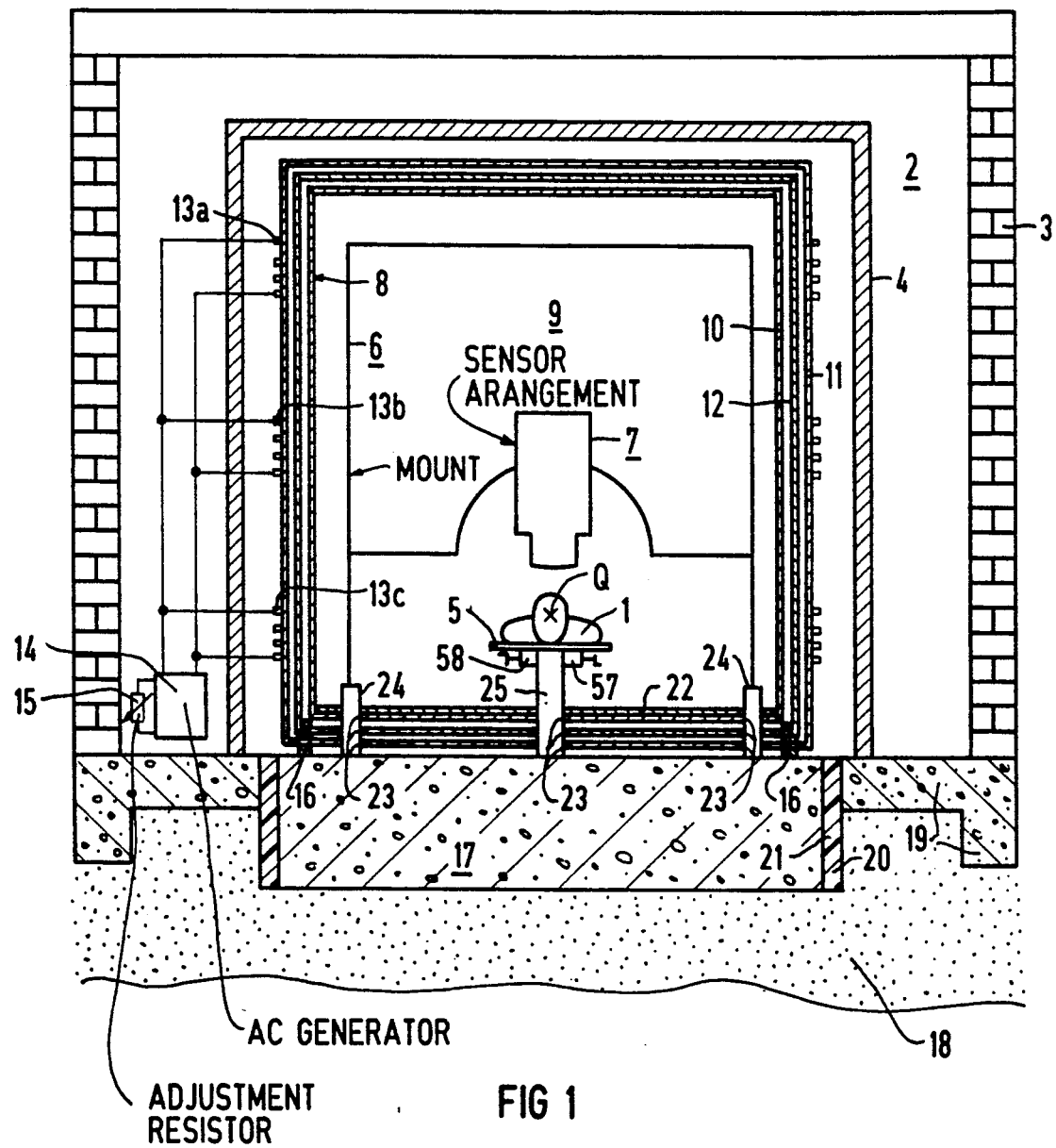
FIG. 1 shows the basic mechanical components of an apparatus constructed in accordance with the principles of the present invention in a partially sectioned side view.

FIG. 1 shows an apparatus of the invention for measuring weak, location-dependent and time-dependent biomagnetic fields that emanate from sources situated in a human patient 1 provided as the examination subject. The apparatus, however, is also suitable for measurements of examination subjects composed of inert matter. The apparatus of the invention, referenced 2 overall, is situated in a building 3 and is surrounded by an outside wall 4. The outside wall 4, for example, can be masonry or formed of rigid plaster sheets or manufactured of sound-damping material, and predominantly serves the purpose of protecting the apparatus 2 against vibration and mechanical damage from the outside. The apparatus 2 includes a bearing means for the patient 1 such as a patient support 5, and a sensor arrangement 7 (schematically indicated with single lines) suspended over the patient 1 by a holder 6 (also schematically indicated with single lines). This sensor arrangement 7 serves the purpose of measuring magnetic fields emanating from sources situated inside of the patient 1. In the embodiment of FIG. 1, the sensor arrangement is aligned to a source Q situated in the skull of the patient 2. The apparatus also includes a shielded room 8 shaped roughly cubically which surrounds the patient support 5 with the patient 1 lying thereon and which also surrounds the sensor arrangement 7. The measuring space 9 situated in the interior of the shielded room 8 is magnetically shielded by this shielded room 8.

The shielded room 8 is constructed of three shells, with the inner shell 10 and the outer shell 11 respectively formed of mu-metal, and the middle shell 12 composed of aluminum. The shielded room 8 has a shielding factor of at least 10 for magnetic alternating fields having a frequency of 0.5 Hz, a shielding factor of at least 100 for magnetic alternating fields having a frequency of 5 Hz, and a shielding factor of at least 1000 for magnetic alternating fields having a frequency of 50 Hz and above. The shielded room 8 has a shielding factor of at least 1,000 for high-frequency alternating fields. The inhomogeneity of the magnetic residual field present in the measuring space 9 under normal ambient conditions is less than 100 nT/m. The outer shell 11 is not absolutely necessary to achieve the desired data and therefore could be eliminated.

The shielded room 8 is surrounded by coils 13a, 13b, 13c that are connected to an AC generator 14 and form a demagnetization means therewith so that the shielded room 8 can be charged with a demagnetization field that is continuously reducible for the demagnetization of the shielded room 8 over at least four orders of magnitude, proceeding from the saturation field strength for mu-metal. This is indicated by a setting resistor 15 connected to the AC generator 14.

The shielded room 8 is rigidly connected to a high-mass foundation base 17 via one or more mounts 16. The mass of the foundation base 17 should be on the order of magnitude of 10 to 20 tons inclusive. It is preferably composed of iron-free concrete. The cuboid foundation base 17 is placed on a sand bed 18. The building 3 has a foundation 19 having a bottom plate that is mechanically separated from the foundation foot 17 by an interspace 20. The interspace 20 is filled with an expanded plastic 21. This assures that mechanical vibrations from outside the building 3 which, for example, are produced by street traffic, are not directly transmitted to the foundation base 17.

The shielded room 8 has a bottom plate 22 that is attached to the inner shell 10 of the shielded room 8 in the region of the floor thereof. The shells 10, 11, 12 and the bottom plate 22 have a plurality of recesses 23 in the region of the floor of the shielded room 8, through which posts 24 and 25 respectively extend. The posts 24 and 25 consist of an electrically insulating material, for example wood, ceramic or plastic, and have their lower ends respectively firmly anchored at the foundation foot 17. The mount 6 for the sensor arrangement 7 is secured to a first plurality of posts, namely to the posts 24. The patient support 5 is secured to a second plurality of posts, namely to posts 25 of which only one can be seen in FIG. 1.

Movements of the patient lying on the patient support 5 must thus first be conducted via the posts 25 on to the foundation base 17 before they can be transmitted from the latter via the posts 24 to the mount 6 and from the mount 6 to the sensor arrangement 7. The same applies inversely for potential vibrations of the sensor arrangement 7. As a consequence of the large mass of the foundation base 17, thus, motions of the sensor arrangement 7 attached to the mount 6 relative to the patient support 5 or relative to the patient 1 lying thereon are largely suppressed. Vibrations that are produced by a physician walking on the bottom plate 22 can likewise be transmitted onto the sensor arrangement 7 or to the patient support 5 only via the mass of the foundation base 17. When a transmission of vibrations of the bottom plate 22 to the shielded room 8 is undesired, the bottom plate 22 can likewise be directly connected to the foundation base 17 via further posts in a similar way.

Figure 2:
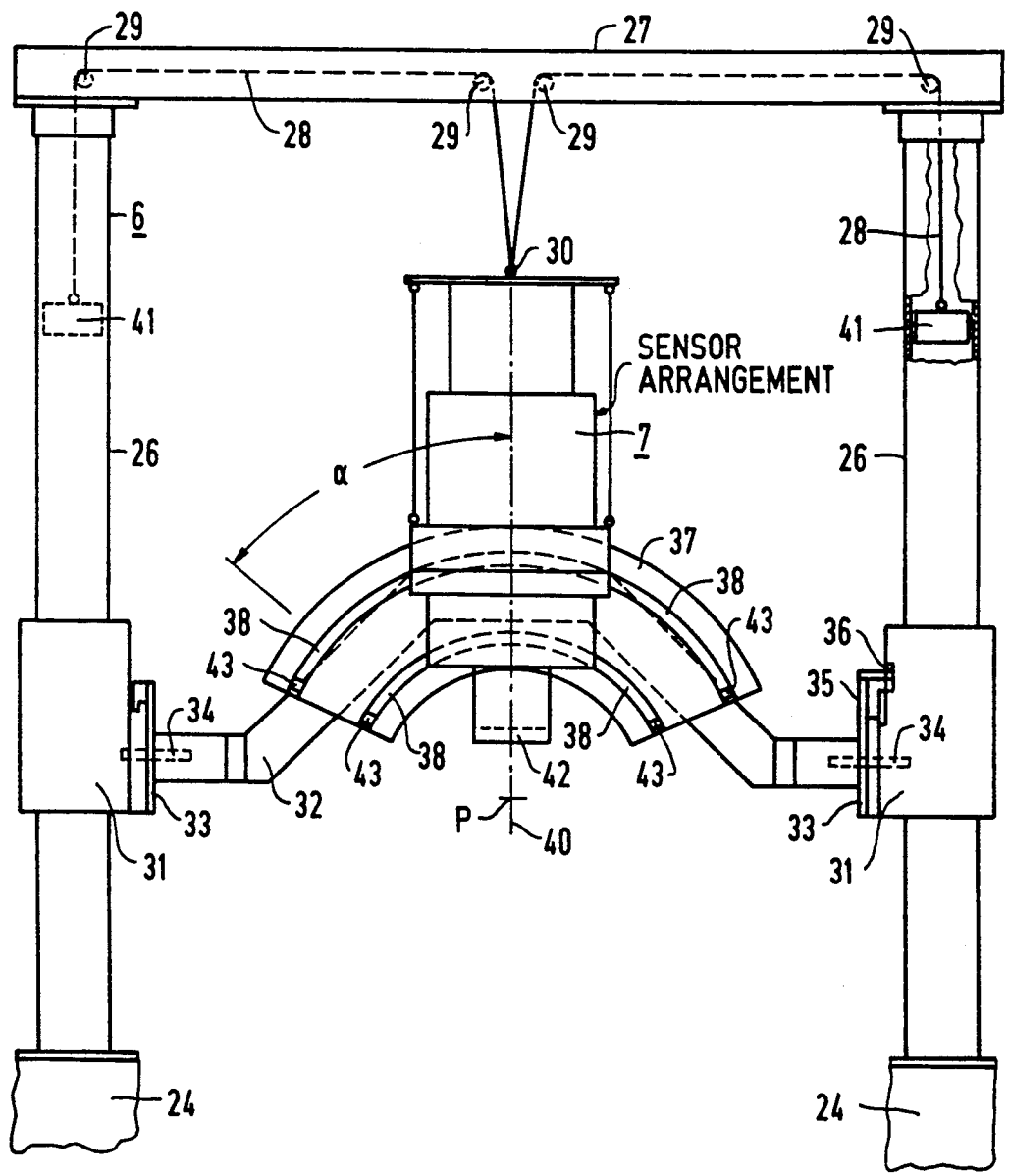
FIG. 2 is a side view of the holder for the sensor arrangement in the apparatus of FIG. 1.
Figure 3:
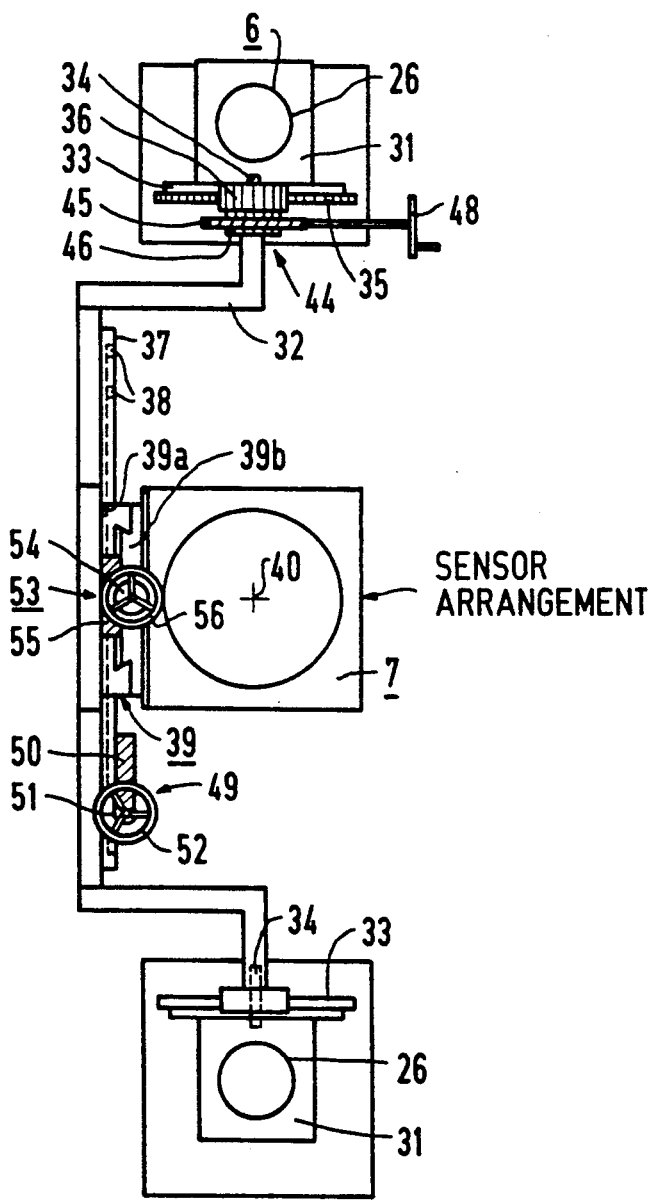
FIG. 3 is a plan view of the holder of FIG. 2.

When a mount according to FIGS. 2 and 3 is provided for the sensor arrangement 7, the distance changes occurring between the sensor arrangement 7 and the patient support 5 in a measurement as a consequence of mechanical excitation are less than 100 μm. Distance changes of this size lead to field changes of at most $2 \times 10^{-13}$T in a residual field having an inhomogeneity of 100 nT/m, given the condition that the sensor arrangement 7 contains gradiometers that are balanced to $2 \times 10^{-2}$. These field changes lie below the signal strength of most biomagnetic signals.

FIGS. 2 and 3 show the mount 6 for the sensor arrangement 7, which includes two vertical columns 26 whose lower ends are rigidly connected to the posts 24 and which have upper ends connected to one another via a cross-stay 27. The columns 26 are hollow and are thereby each suitable for accepting an internally displaceable counter-weight 41. Each counter-weight 41 is connected to a common eyelet 30 via a cable 28 which runs through the interior of the hollow cross-stay 27 via deflection rollers 29. The common eyelet 30 is secured to the sensor arrangement 7.

A running box 31 is attached to each of the columns 26 in height-displaceable fashion. The running boxes 31 are connected to one another via a shackle 32. The shackle 32 has a circular disk segment 33 at each of its ends which is seated rotatable around a pin 34 secured to the running box 31. A gear rim 35, which engages a gear wheel drive 36 is provided at the circumference of one of the circular disk segments 33. The shackle 32 can thus be pivoted around an axis proceeding through the pin 34.

A circular ring segment 37 is attached in the center of the shackle 32. The circular ring segment 37 is provided with one or a plurality of parallel grooves 38 in the shape of circular segments. The sensor arrangement 7 is pivotably seated in the grooves 38 via tenon blocks secured to it. The swivel angle with respect to the vertical is referenced α. The adjustment by the angle α ensues via a spur gear. The circular ring segment 37 is aligned parallel to the shackle plane during swivel.

The sensor arrangement 7 is displaceable in height relative to the circular ring segment 37 via a carriage 39. The displacement thereby always ensues in radial direction, i.e. in the direction of the radius of the circular ring segment 37. Further, the sensor arrangement 7 can be turned around its central axis 40 via a bearing (not shown).

The unit composed of sensor arrangement 7, circular ring segment 37, shackle 32 and running boxes 31 can be displaced in height, i.e. relative to the stand columns 26, with the assistance of the above-described counter-weights 41 in combination with the cables 28 and the deflection rollers 29. In addition to serving the purpose of mechanical reinforcement, the cross-stay 27 thus simultaneously serves as bridge for weight compensation between the weight of the sensor arrangement 7 and the counter-weights 41 gliding in the columns 26. The height adjustment serves the purpose of bringing the sensor surface 42 (indicated with broken lines) of the sensor arrangement 7 immediately against the patient 1.

The sensor arrangement 7 is displaceable by the angle α along the grooves 38. The maximum angle α thereby amounts to about 50° toward each side. A detent 43 is provided at each of the ends in each of the grooves 38. This prevents the swiveled sensor arrangement 7 from striking the stand column 26. The sensor surface 42 remains aligned to the same point P both when pivoting by the angle α as well as when turning the shackle 32. The point is usually placed in the head or in the thorax of the patient 1 at a location proximate a source Q of magnetic signals. The distance between the sensor surface 42 and the point P can be varied with the assistance of the carriage 39.

As can be seen in FIG. 3, the gear wheel drive 36 has a worm gearing 44 allocated to it on at least one side. The worm gearing 44 includes a worm wheel 45, a worm 46 as well as a hand wheel 48 for adjustment. A worm gearing 49 (including worm wheel 50, worm 51 and hand wheel 52) is also provided between the carriage 39 and the circular ring segment 37, the swivel angle α being capable of being adjusted and locked with the assistance of this worm gearing 49. FIG. 3 shows that the carriage 39 is subdivided into two parts 39a and 39b. The part 39a is seated in the groove 38 and the part 39b is displaceable in a radial direction relative to the part 39a (for example, via a dovetail guide). The angle α derives by displacing the part 39a along the groove 38, as a result the part 39b is also moved. A further worm gearing 53 including the worm wheel 54, the worm 55 and the hand wheel 56 is present for radial displacement of the part 39b relative to the part 39a.

In addition to the adjustment possibilities of the sensor arrangement 7 relative to the patient support 5 that derive from the above-described fashioning of the mount 6, further adjustment possibilities of the components relative to one another exist in that the patient support 5 is displaceable in a plane proceeding parallel to the floor of the shielded room 8 in the direction of its longitudinal axis and transversely thereto. This displacement is achieved with the assistance of two manually actuatable drives 57 and 58. Further details regarding these drives are not shown, those skilled in the art being familiar with suitable mechanisms. The described fashioning of the mount 6 and of the patient support 5 permits alignment of the sensor surface 42 of the sensor arrangement 7 to desired body zones of the patient 1. The position of the patient support 5 together with patient 1 relative to the sensor arrangement 7 can be acquired in a known fashion, for example with an arrangement of readable measuring scales that are allocated to the worm gearings 44, 49, 53 or that are attached to the patient support 5 in a known manner. A scale 88 and a pointer 89 for identifying the position of the patient support 5 in the longitudinal direction thereof with reference to the sensor arrangement 7 are shown by way of example in FIG. 6. The scale 88 thereby assumes a defined position relative to the sensor arrangement 7.

The mount 6 and the patient support 5 are fashioned overall of non-ferromagnetic materials.

Figure 4:
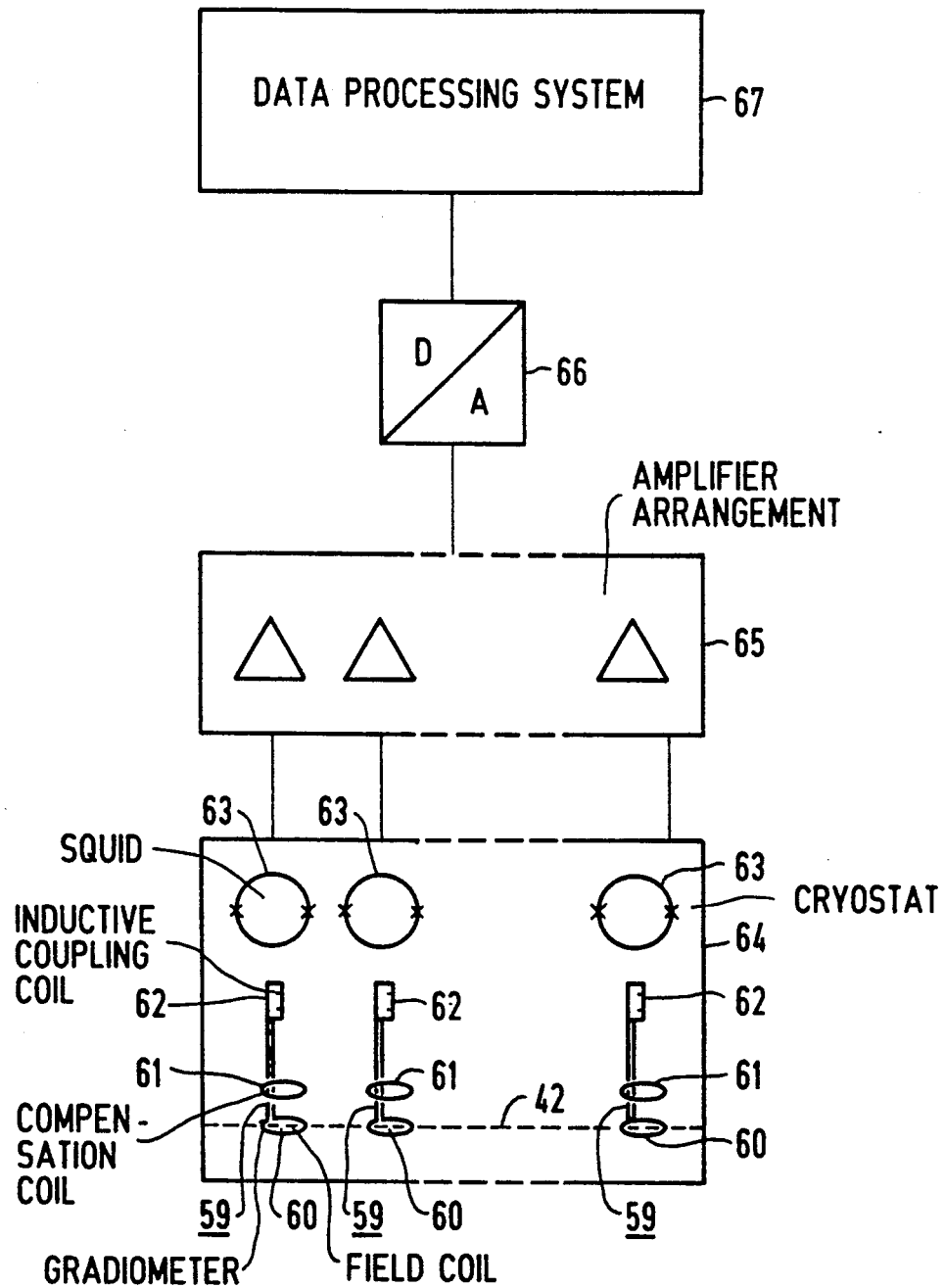
FIG. 4 is a schematic block diagram of the sensor arrangement used in the apparatus constructed in accordance with the principles of the present invention.

The structure of the sensor arrangement 7 is shown in schematic fashion in FIG. 4. The sensor arrangement 7 includes an array of 12 gradiometers of the first order, each of which bears reference numeral 59, with only some of the gradiometers 59 being shown in FIG. 4. The gradiometers 59 are axial gradiometers. As is known, these include a respective field coil 60 and a compensation coil 61 connected thereto, with the compensation coil 61 wound in a direction opposite the corresponding field coil 60, and both having a common center axis. The compensation coil 61 of each gradiometer 59 is arranged in a plane that proceeds parallel to the plane of the corresponding field coil 60. The voltages induced in the field coil 60 and in the compensation coil 61 cancel in accord with the balancing for magnetic fields that arise at a greater distance from a gradiometer constructed in such fashion. When, however, the source of a magnetic field lies in the proximity of such a gradiometer 59—as is the case for a source present in an examination subject, for example the patient 1 situated in the proximity of the sensor arrangement 7—, then the voltage induced in the field coil 60 is considerably higher than the voltage induced in the compensation coil 61. It is advantageous that the field strength decreases very quickly in the near range of the source. The gradiometers 59 provided in the decribed sensor arrangement have a sensitivity reduced to $2 \times 10^{-2}$ for uniform magnetic fields. Such gradiometers can be realized with little outlay.

Each of the field coils 60 of each of the gradiometers 59 respectively surround an area of at least 3.5 cm$^2$. When the field coils 60—as shown in FIG. 4—have an approximately circular shape, they have a diameter of at least 2.1 cm. Field coils 60 and compensation coils 61 have a spacing of 7 cm.

The gradiometers 59 are each respectively connected to a coil 62 that serves the purpose of respectively inductively coupling the gradiometers to a DC-SQUID of an array of twelve SQUIDs. As already implied by the name, the SQUIDs utilize the Josephson effect, and operate in the superconducting condition. The gradiometers 59 and the SQUIDs 63 are arranged in a schematically indicated thermal container, referred to as a cryostat, that bears reference character 64. This contains liquid helium which, as is known, has a temperature of about 4.2°K. The field coils 60 of the gradiometers 59 are arranged in a sensor surface 42 (indicated with broken lines) immediately behind the wall of the cryostat 64 lying opposite them. Further details regarding the structure of such sensor arrangement 7 may be derived from the aforementioned publication of Crum et al, as well as from H. Jablonski, "Zum Stand der kommerziell zur Verfuegung stehenden SQUID-Messsysteme zur Messung biomagnetischer Signale", Ergebnisberichte zum Programm "Forschung und Entwicklung im Dienste der Gesundheit-Biomagnetische Signale/SQUID-Messsysteme", DFVLR-NT 1/84 1, pages 29 through 42.

The individual SQUIDs 63 of the array are connected to an amplifier arrangement 65 (described in detail below) which is a component of an electronic means for amplifying and evaluating the signals of the gradiometers 59. An analog-to-digital converter 66 is connected to the output of the amplifier arrangement 65. The output of the converter 66 is in turn connected to an electronic data processing system 67 which, among other things, serves the purpose of evaluating the signals derived from the gradiometers 59. As indicated in FIG. 4, the amplifier arrangement 65 contains a plurality of amplifier channels corresponding in number to the plurality of gradiometers 59 or SQUIDs 63, with each amplifier channel connected to one of the DC-SQUIDs 63.

Figure 5:
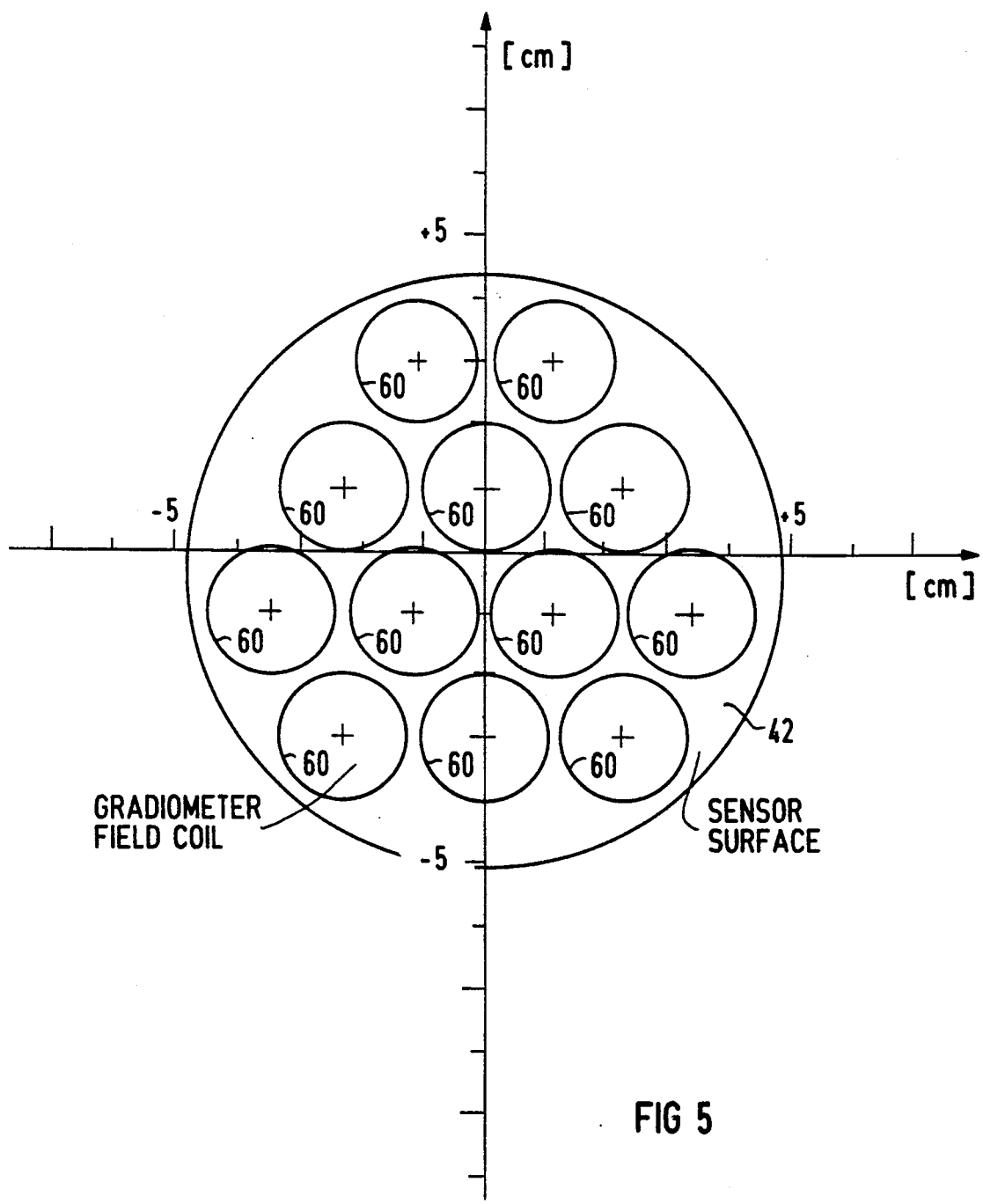
FIG. 5 shows the arrangement of axial gradiometers contained in the sensor arrangement of FIG. 4 in the sensor surface.

The arrangement of 12 gradiometers in the sensor surface 42 of the sensor arrangement 7 is schematically indicated in plan view in FIG. 5. According to this figure, the selected arrangement yields a good utilization of the area available, and has an approximately circular shape and a diameter of about 10 cm. The field coils 60 of the gradiometers indicated in FIG. 5 each have a diameter of 2.1 cm and thus surround an area of 35 cm$^2$.

Figure 6:
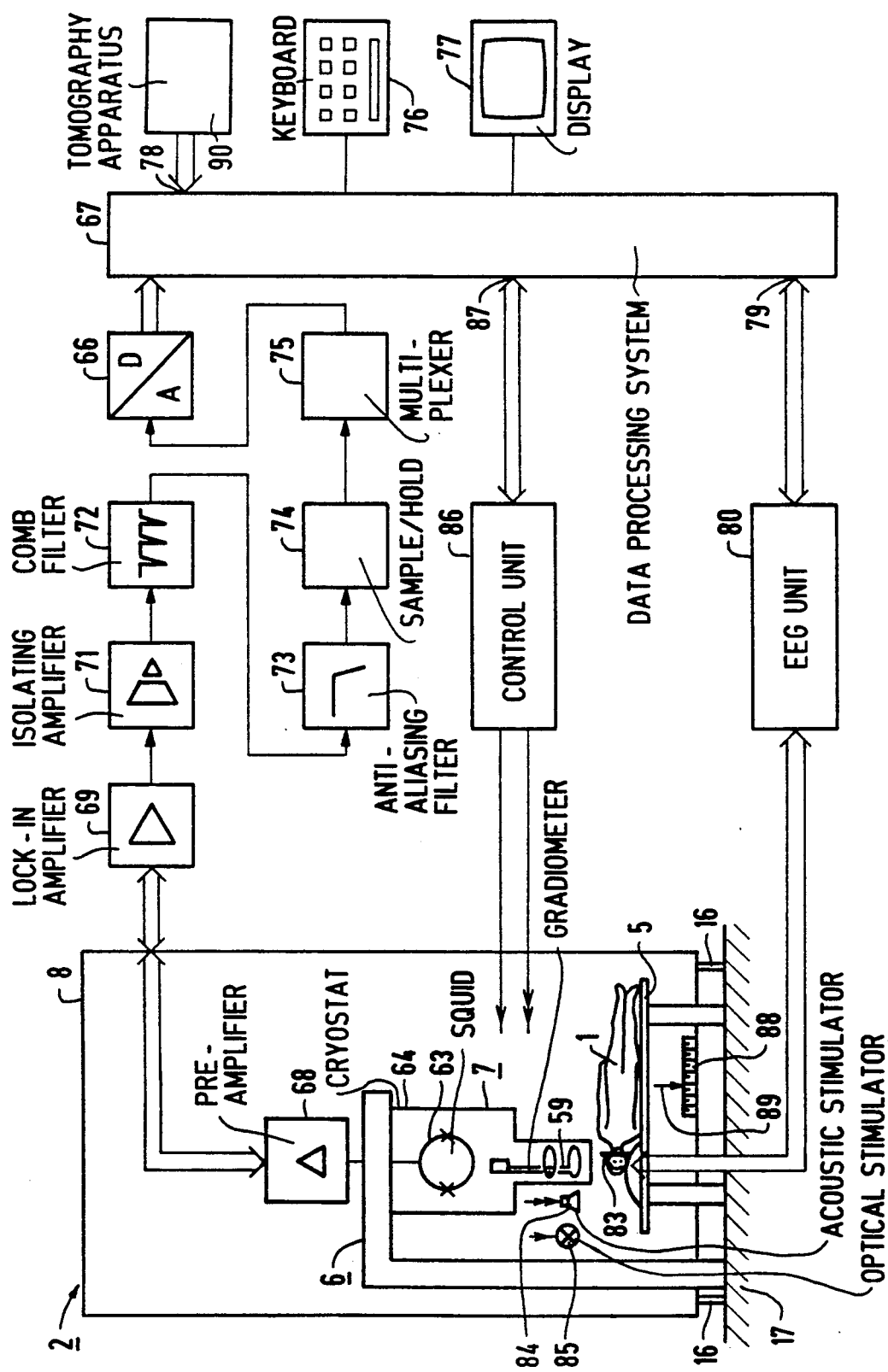
FIG. 6 is a schematic block diagram of the apparatus of FIG. 1, including the electric components.

Further details regarding the amplifier arrangement 65 are shown in FIG. 6 in which the apparatus of the invention is shown with all mechanical and electronic components. Only one gradiometer 59 with the associated DC-SQUID 63 and the following amplifier channel of the amplifier arrangement 65 are shown in FIG. 6. The remaining channels are identically constructed. According to FIG. 6, an amplifier channel has a pre-amplifier 68 arranged in the region of the sensor arrangement 7, the pre-amplifier 68 being connected to the SQUID corresponding to the respective channel. The output signal of the pre-amplifier 69 proceeds to a lock-in amplifier 68 that holds the respective input signal to a constant level and whose feedback signals represent the output signal. The lock-in amplifier 69 is followed by an isolating amplifier 71 which undertakes a voltage separation between the amplifiers to avoid ground loops.

For suppressing disturbances caused by the electrical network, the isolating amplifier 71 of each amplifier channel is followed by a comb filter 72 that is tuned to the frequency of the electrical line and to the whole multiples thereof. The comb filter 72 is followed by a steep-edged anti-aliasing filter 73 from which the signals proceed to a sample-and-hold circuit 74. The sample-and-hold circuits 74 are connected via a 12-to-1-multiplexer 75 to the analog input of the analog-to-digital converter 66 that has its digital output connected to the data processing system 67. The sample-and-hold circuits 74, the 12-to-1-multiplexer 75 and the analog-to-digital converter 66 receive the respectively required control signals from the data processing system 67. The anti-aliasing filters 73 each have a time constant for avoiding artifacts that corresponds to at least twice the conversion time of the analog-to-digital converter 66 multiplied by twelve (the number of channels). There is also the possibility of providing a separate analog-to-digital converter for each of the amplifier channels of the amplifier arrangement 65. The multiplexer 75 can then be omitted. The time constants of the anti-aliasing filters 73 can then be selected such that they correspond to at least twice the conversion time of the analog-to-digital converters. A limit frequency higher by a factor corresponding to the number of channels (twelve in the case of the exemplary embodiment), thus derives in comparison to the arrangement set forth above.

As is known, the data processing system 67 includes a central processing unit (CPU), a program memory and a data memory. A keyboard 76 is connected to the data processing system 67 as an input means and a display 77 is connected thereto as an output means for results of the evaluation of the signals derived from the gradiometers 59. A printer and/or plotter (not shown) can also be provided as the output means. The data processing system 67 also has an interface 78 via which it can be connected to a tomography apparatus, schematically indicated at 90, for example a nuclear magnetic resonance tomography apparatus, so that, in addition to the data acquired from the signals of the sensor arrangement 7 by the analog-to-digital converter 66, preferably three-dimensional anatomical images of the examination subject produced with the tomography apparatus can be stored in digitized form in the data memory of the data processing system 67.

The data processing system 67 also includes an interface 79 to which a means (schematically indicated in FIG. 6) for measuring at least one physiological function of the patient 1, for example a known EEG apparatus 80, is connected. The data supplied by the EEG apparatus 80 are likewise stored in the data memory of the data processing system 67 in digitized form. The patient 1 assumes a side position in FIG. 6, whereby his skull is supported by a pillow.

As mentioned, the position of the patient support 5 relative to the sensor arrangement 7 can be acquired, for example by reading scales and can be input into the data processing system 67 with the keyboard 76. An automatic acquisition via known electrical or optical position sensors including transmission to the data processing system 67 is also possible.

A bite down piece 83 schematically indicated in FIG. 6, which is rigidly connected to the patient support 5 and on which the patient 1 lying on the patient support 5 bites during the examination, is provided to be able to produce a defined spatial position of the patient 1 relative to the patient support 5. Data regarding the position of the bite-down piece 83 relative to the patient support 5 are stored in the data processing system 67, so that the latter is able to calculate the spatial position of the skull of the patient 1 relative to the sensor arrangement 7 on the basis of this data and on the basis of the data relating to the spatial position of the sensor arrangement 7 relative to the patient support 5. When body parts other than the skull of the patient 1 are to be examined, other structure suitable for producing a defined position of the patient 1 relative to the patient support 5 can be employed instead of the bitedown piece 83.

As schematically indicated in FIG. 6, means for stimulating the patient's senses are provided in the region of the skull of the patient 1. A loudspeaker 84 and a light signal 85 are used. Both are actuated in a suitable way for acoustic and/or optical stimulation of the senses of the patient 1, by control electronics 86 connected to the data processing system 67 via an interface 87.

Figure 7:
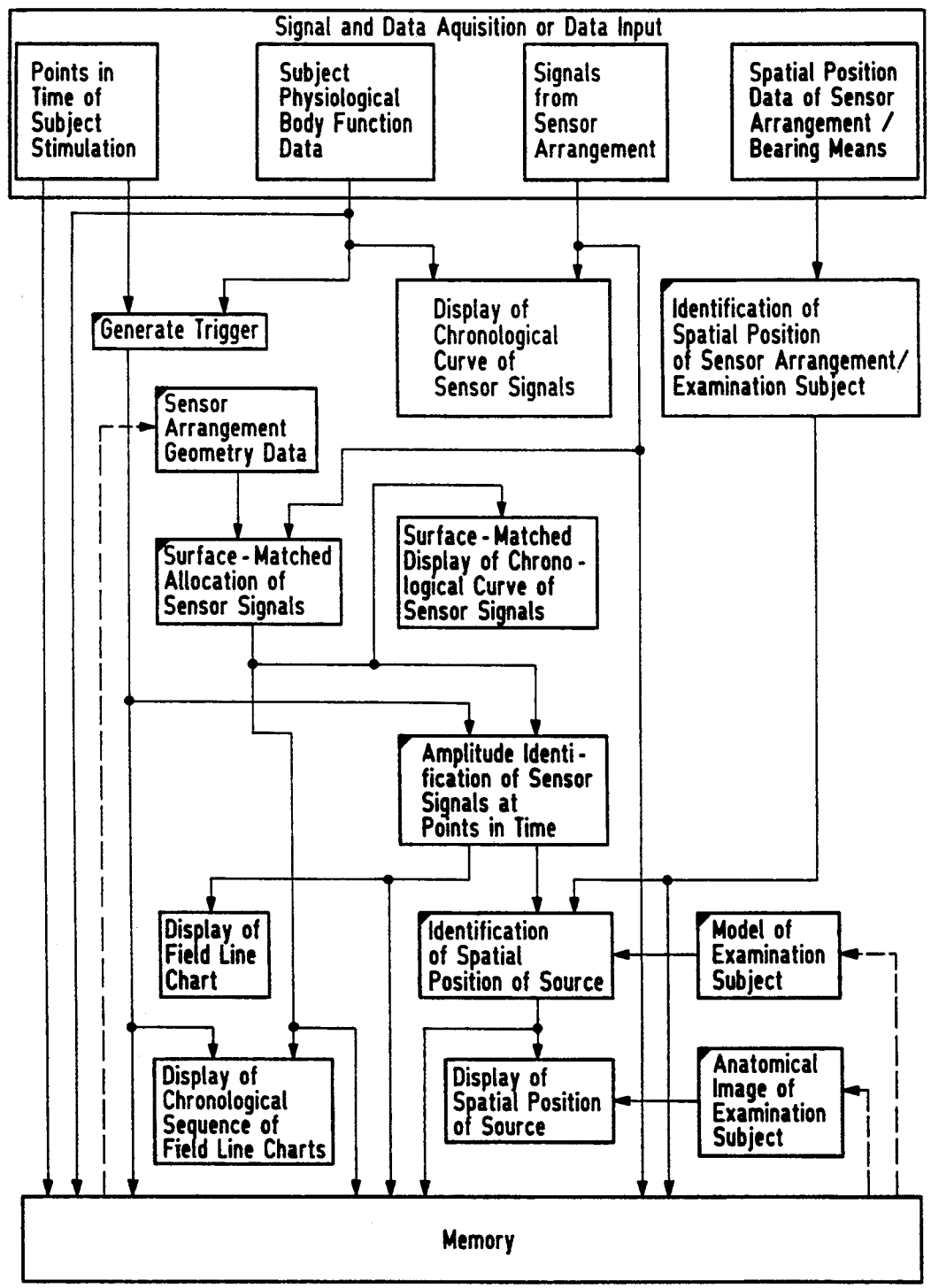
FIG. 7 is a flow chart of an operating method for the apparatus of FIGS. 1 through 6.

A method for operating the apparatus according to FIGS. 1 through 6 is shown in FIG. 7 in the form of a flow chart. In accord therewith, the signals derived from the sensor arrangement 7, the data associated with the physiological function of the patient 1, and data which indicate the points in time at which a stimulation of the patient 1 ensues are acquired in the data processing system 67, and data regarding the position of the sensor arrangement 7 and the patient support 5 relative to one another are entered into the data processing system 67 or are acquired given automatic sensors. The signals derived from the sensor arrangement as well as the data pertaining the physiological function of the patient 1 are individually portrayed in their chronological path or are portrayed for a plurality of channels of the sensor arrangement 7. If required, the data are allocated to the positions of the individual gradiometers 59 and are portrayed after surface-matched allocation with the assistance of data regarding the geometry of the sensor arrangement 7 which are stored in the data processing system 67. Upon additional employment of the data regarding the points in time at which a stimulation of the patient 1 ensues, as warranted, further signal parameters such as, for example, the amplitude, can be derived from these results and can be portrayed as a field line chart. By using the data regarding the spatial position of the patient 1 relative to the sensor arrangement 7 calculated with the data processing system 67 and a stored model of the examined body region of the patient 1, moreover, the spatial position of the source Q can be identified and can be portrayed in combination with an anatomical image of the examined body region of the patient 1 that is acquired with an imaging method and is stored in the data processing system 67.

The signals and data acquired with the data processing system 67 as well as signals and data derived therefrom (identified in FIG. 7 by blocks in the flow chart identified with a blackened triangle) can be stored in a memory, for example a magnetic disk or the like, that is allocated to the data processing system 67.

Figure 8:
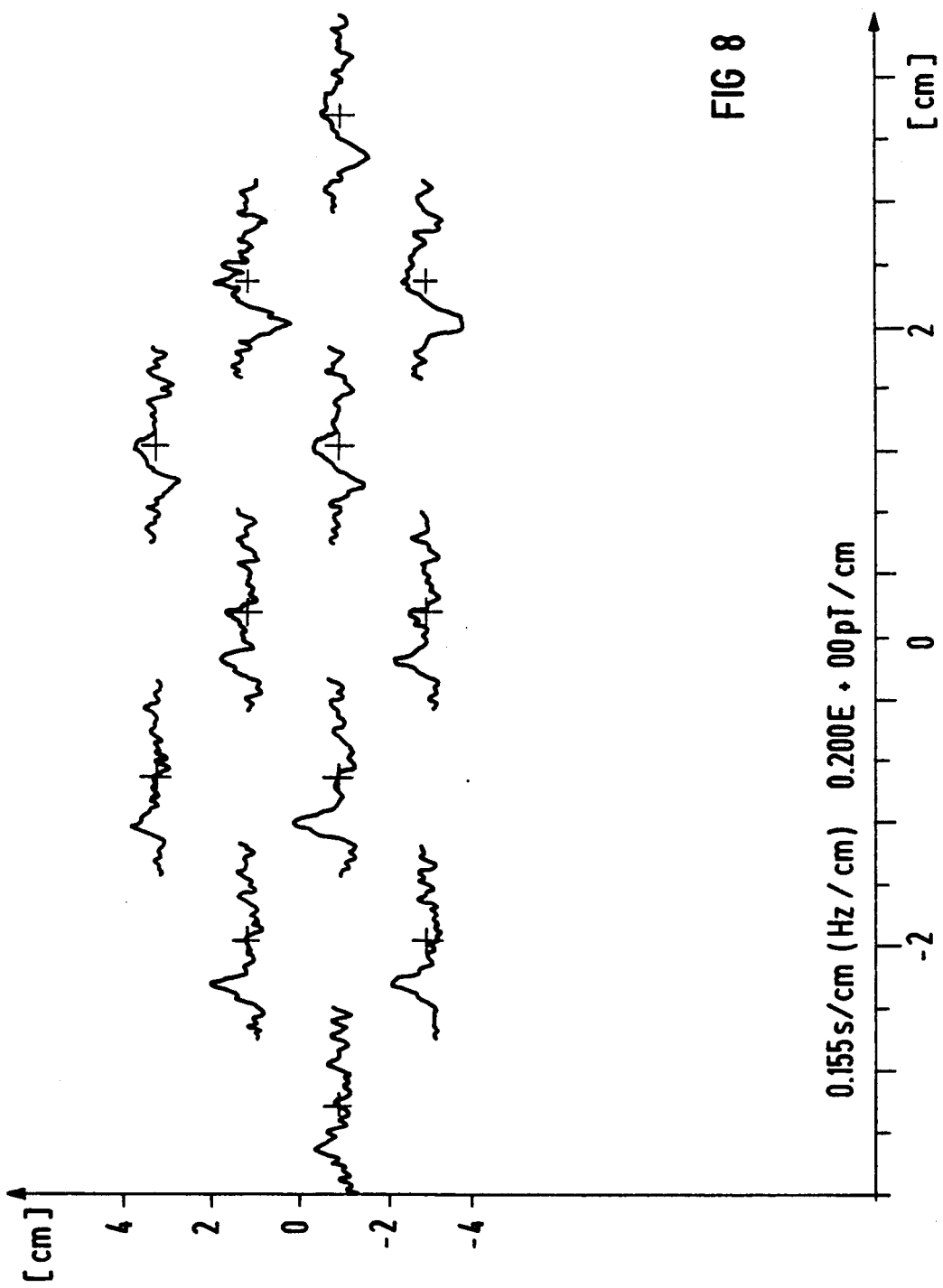
FIGS. 8 through 10 show examples of results obtained with the apparatus of FIGS. 1 through 6 with the implementation of the method of FIG. 7.
Figure 9:
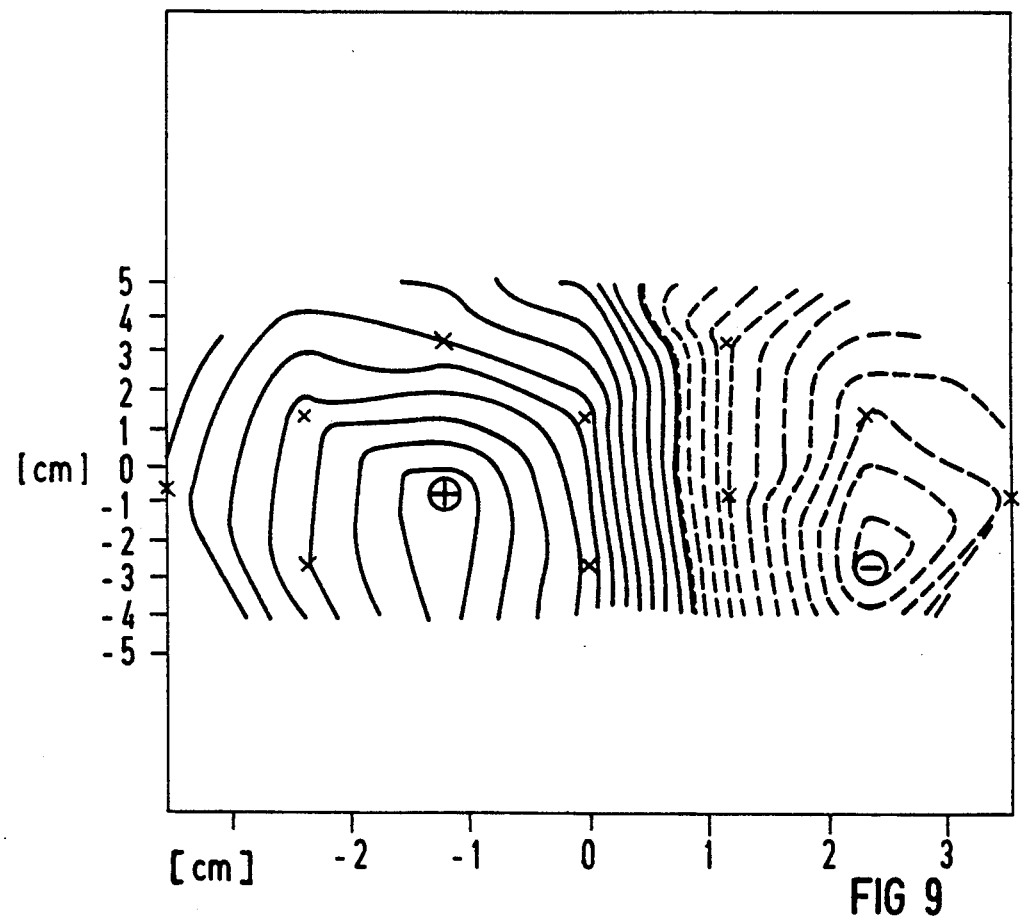
Figure 10:
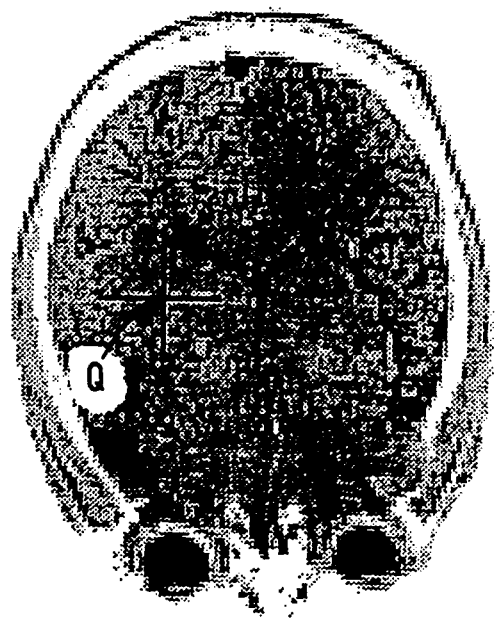

FIGS. 8 through 10 show measured results as obtained with the apparatus according to FIGS. 1 through 6 when this is operated in accord with the above-described method.

In detail, FIG. 8 shows the chronological course of the magnetic flux density of a source. The chronological curves of the flux density as obtained with the individual gradiometers 59 of an arrangement of FIG. 5 are separately illustrated. The corresponding curves are shown in an arrangement relative to one another in FIG. 8 that corresponds to the arrangement of the gradiometers 59 of FIG. 5.

FIG. 9 shows a field line chart in which lines of identical magnetic flux density are entered for a plane that assumes a defined position relative to a source Q. The field line chart thereby reproduces the conditions for a defined point in time within the measuring time span.

FIG. 10, finally, shows a tomogram of an examination subject, namely of the skull of a human patient in which the position of a source Q is entered that was acquired with nuclear magnetic resonance tomography. A two-dimensional image is shown, however, there is also the possibility of entering the identified, spatial position of a source Q in three-dimensional images of an examination subject.

Although modifications and changes may be suggested by those skilled in the art, it is the intention of the inventors to embody within the patent warranted hereon all changes and modifications as reasonable and properly come within the scope of their contribution to the art.

We claim as our invention:

1. An apparatus for measuring weak, location-dependent and time-dependent magnetic fields emitted from a source situated in an examination subject, said apparatus comprising:

bearing means for supporting said examination subject;

a sensor arrangement including an array of at least ten identical axial gradiometers of the first order, each gradiometer having a field coil and a corresponding compensation coil, with the field coils of the gradiometer being disposed in a substantially circular sensor surface, an array of DC-SQUIDS corresponding in number to the number of said gradiometers, each gradiometer being inductively coupled to one of said DC-SQUIDs and each DC-SQUID having an analog output, and a vessel containing said gradiometers and said DC-SQUIDs having a temperature therein at which said gradiometers and said DC-SQUIDs are superconducting;

mounting means for mounting said sensor arrangement;

means for adjusting said sensor arrangement, disposed in said mounting means, for adjusting said bearing means and said sensor arrangement relative to each other so that said sensor arrangement can be positioned relative to a selected zone of said examination subject;

a room surrounding said bearing means and said sensor arrangement, said room including means for shielding an interior of said room from magnetic fields, said means for shielding having a shielding factor of at least 10 for magnetic alternating fields having a frequency of 0.5 Hz, a shielding factor of at least 100 for magnetic alternating fields having a frequency of 5 Hz, and a shielding factor of at least 1,000 for magnetic alternating fields having a frequency of 50 Hz and above, said means for shielding consisting of an inner shell of a low-retentivity material having a relative permeability greater than $10^4$, and an outer shell of aluminum;

electronic means for evaluating signals from said gradiometers, said electronic means including amplifier means for amplifying signals from analog outputs of said DC-SQUIDs, said amplifier means having a plurality of amplifier channels corresponding in number to, and respectively connected to, outputs of said DC-SQUIDS, an analog-to-digital converter connected to an output of said amplifier means, digital data processing means for selectively processing the amplified and converted output signals from said DC-SQUIDs, and means for visually displaying a selected output image constructed by said data processing means.

2. An apparatus as claimed in claim 1, further comprising means for charging said room with a demagnetization field which is continuously reducible over a range of at least four orders of magnitude.

3. An apparatus as claimed in claim 1, wherein said room includes a foundation base and means for attaching said mounting means and said bearing means to said foundation base separately from each other.

4. An apparatus as claimed in claim 1, wherein said amplifier means includes, in each channel, a preamplifier followed by a lock-in amplifier.

5. An apparatus as claimed in claim 4, wherein said amplifier means further includes, in each channel, an isolating amplifier connected between said preamplifier and said lock-in amplifier.

6. An apparatus as claimed in claim 4, wherein said amplifier means further includes, in each channel, an isolating amplifier connected following said lock-in amplifier.

7. An apparatus as claimed in claim 4, wherein said electronic means further includes a comb filter connected to each channel of said amplifier means and tuned to the frequency of the electrical line and to whole-number multiples thereof.

8. An apparatus as claimed in claim 1, further comprising an anti-aliasing filter connected in each channel of said amplifier means preceding said analog-to-digital converter.

9. An apparatus as claimed in claim 1, wherein said examination subject is a life form, said apparatus further comprising means for measuring a physiological function of said life form and for supplying a physiological signal, said physiological signal corresponding to said physiological function, to said data processing means, said data processing means including means for correlating said signals from said gradiometers with said physiological signal to obtain a correlated image, and wherein said means for displaying a selected output image includes means for displaying said correlated image.

10. An apparatus as claimed in claim 1, wherein said examination subject is a life form, said apparatus further comprising means for stimulating the senses of said life form and for supplying a time signal identifying the time of the stimulation of the senses to said data processing systems, said data processing means further including means for correlating said signals from said gradiometers with said time signal to obtain a correlated image, and wherein said means for displaying a selected output image includes means for displaying said correlated image.

11. An apparatus as claimed in claim 1, further comprising:

mechanical means for positioning said examination subject on said bearing means in a defined position relative to said bearing means; and means for identifying the spatial position of said sensor arrangement relative to said bearing means and for supplying signals corresponding thereto to said data processing means.

12. An apparatus as claimed in claim 11, wherein said mecha means is a bite-down plate.

* * * * *